US00PP21543P2

(12) United States Plant Patent
Herold

(10) Patent No.: US PP21,543 P2
(45) Date of Patent: Nov. 30, 2010

(54) ***POLYGONATUM* PLANT NAMED 'ANGEL WING'**

(50) Latin Name: *Polygonatum odoratum*
Varietal Denomination: Angel Wing

(76) Inventor: Roy Herold, 168 Stoney Gate, Carlisle, MA (US) 01741

( * ) Notice: Subject to any disclaimer, the term of this patent is extended or adjusted under 35 U.S.C. 154(b) by 0 days.

(21) Appl. No.: 12/458,167

(22) Filed: Jul. 1, 2009

(51) Int. Cl.
*A01H 5/00* (2006.01)

(52) U.S. Cl. ..... Plt./263.1

(58) Field of Classification Search ..... Plt./373, Plt./263.1
See application file for complete search history.

*Primary Examiner*—Susan B McCormick Ewoldt
(74) *Attorney, Agent, or Firm*—C. A. Whealy

(57) ABSTRACT

A new and distinct cultivar of *Polygonatum* plant named 'Angel Wing', characterized by its compact and upright plant habit; freely clumping and vigorous growth habit; and variegated leaves with relatively wide white-colored margins.

1 Drawing Sheet

Botanical designation: *Polygonatum odoratum.*
Cultivar denomination: 'Angel Wing'.

BACKGROUND OF THE INVENTION

The present invention relates to a new and distinct cultivar of *Polygonatum* plant, botanically known as *Polygonatum odoratum*, and hereinafter referred to by the name 'Angel Wing'.

The new *Polygonatum* plant is a naturally-occurring whole plant mutation of *Polygonatum odoratum* 'Variegated', not patented. The new *Polygonatum* was discovered and selected by the Inventor as a single plant from within a population of plants of 'Variegated' in a controlled greenhouse environment in North Reading, Massachusetts in 1990.

Asexual reproduction of the new *Polygonatum* plant by divisions in a controlled environment in North Reading, Massachusetts since 1995 has shown that the unique features of this new *Polygonatum* plant are stable and reproduced true to type in successive generations.

SUMMARY OF THE INVENTION

Plants of the new *Polygonatum* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Angel Wing'. These characteristics in combination distinguish 'Angel Wing' as a new and distinct cultivar of *Polygonatum:*

1. Compact and upright plant habit.
2. Freely clumping and vigorous growth habit.
3. Variegated leaves with relatively wide white-colored margins.

Plants of the new *Polygonatum* differ primarily from plants of the parent, 'Variegated', in the following characteristics:

1. Plants of the new *Polygonatum* have shorter rhizomes than plants of 'Variegated'.
2. Plants of the new *Polygonatum* have shorter stems with shorter internodes than plants of 'Variegated'.
3. Leaves of plants of the new *Polygonatum* have broader white-colored margins than leaves of plants of 'Variegated'. Plants of the new *Polygonatum* can be compared to plants of *Polygonatum odoratum* 'Double Stuff', disclosed in U.S. Plant Pat. No. 19,624. Plants of the new *Polygonatum* differ primarily from plants of 'Double Stuff' in stem color as plants of 'Double Stuff' have red-colored stems.

BRIEF DESCRIPTION OF THE PHOTOGRAPHS

The accompanying colored photographs illustrate the overall appearance of the new *Polygonatum* plant, showing the colors as true as it is reasonably possible to obtain in colored reproductions of this type. Colors in the photographs may differ slightly from the color values cited in the detailed botanical description which accurately describe the colors of the new *Polygonatum* plant.

The photograph at the bottom of the sheet comprises a side perspective view of a typical plant of 'Angel Wing'.

The photograph at the top of the sheet is a close-up view of typical leaves of 'Angel Wing'.

DETAILED BOTANICAL DESCRIPTION

The aforementioned photographs and following observations, measurements and values describe plants grown in Lancaster, Pa. in a polyethylene-covered greenhouse during the winter and spring. During the production of the plants, day temperatures ranged from 2° C. to 21° C. and night temperatures ranged from 2° C. to 13° C. Plants were ten months old when the photographs and the description were taken. In the detailed description, color references are made to The Royal Horticultural Society Colour Chart, Fifth Edition, 2007, except where general terms of ordinary dictionary significance are used.

Botanical classification: *Polygonatum odoratum* 'Angel Wing'.

Parentage: Naturally-occurring whole plant mutation of *Polygonatum odoratum* 'Variegated', not patented.

Propagation:

*Type.*—By divisions.

*Root description.*—Medium in thickness, fleshy; white in color.

*Rhizome description.*—Length: About 9 cm. Diameter: About 1.2 cm. Texture: Smooth, glabrous. Color: Close to 158A.

Plant description:

*Type of plant.*—Herbaceous perennial.

*Plant and growth habit.*—Compact and upright plant habit; freely clumping and vigorous growth habit; leaves developing from rhizomes.

*Plant height.*—About 32 cm.

*Plant width.*—About 29 cm.

*Internode length.*—About 2.5 cm to 3.5 cm.

*Stem texture.*—Smooth, glabrous.

*Stem color.*—Close to 144B.

Foliage description:

*Arrangement.*—Alternate, simple; sessile.

*Length.*—About 7.4 cm.

*Width.*—About 4.5 cm.

*Shape.*—Elliptical.

*Apex.*—Acute.

*Base.*—Equilateral to cuneate.

*Margin.*—Entire.

*Venation pattern.*—Pinnate; arcuate.

*Texture, upper and lower surfaces.*—Smooth, glabrous.

*Color.*—Developing leaves, upper surface: Close to 137B. Developing leaves, lower surface: Close to 191A. Fully developed leaves, upper surface: Centers, close to 137A; towards the margins, close to 155A; venation, same colors as surface colors. Fully developed leaves, lower surface: Centers, close to N138C; towards the margins, close to 155B; venation, same colors as surface colors.

Flower description: Flower development has not been observed on plants of the new *Polygonatum.*

Disease/pest resistance: Plants of the new *Polygonatum* have not been observed to be resistant to pathogens and pests common to *Polygonatums.*

Garden performance: Plants of the new *Polygonatum* have exhibited good garden performance and to tolerate rain and wind and have been observed to tolerate temperatures ranging from −25° C. to 40° C.

It is claimed:

1. A new and distinct *Polygonatum* plant named 'Angel Wing' as illustrated and described.

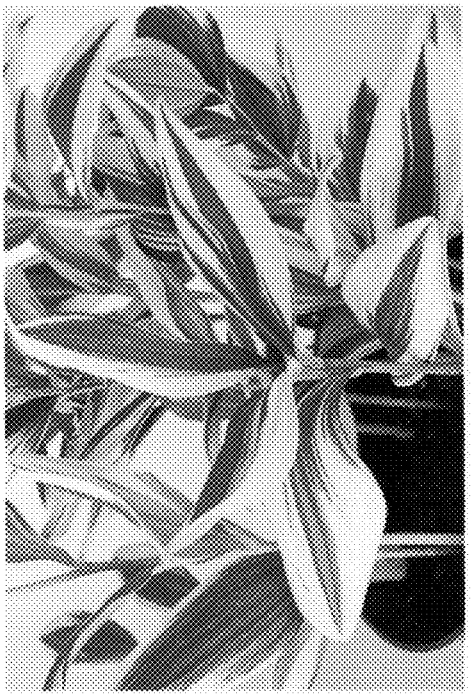
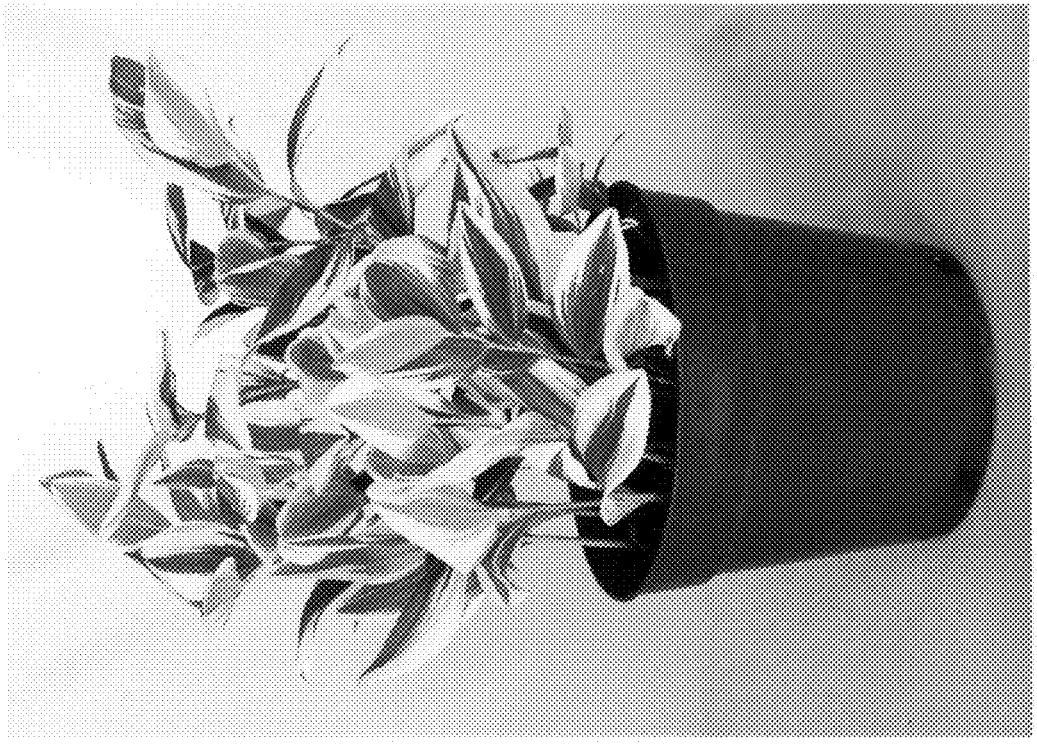

* * * * *